(12) United States Patent
Plumptre et al.

(10) Patent No.: US 8,585,656 B2
(45) Date of Patent: Nov. 19, 2013

(54) DOSE SETTING MECHANISM FOR PRIMING A DRUG DELIVERY DEVICE

(75) Inventors: David Aubrey Plumptre, Worcestershire (GB); Christopher John Jones, Gloucestershire (GB); Robert Frederick Veasey, Warwickshire (GB)

(73) Assignee: Sanofi-Aventis Deutschland GmbH, Frankfurt Am Main (DE)

( * ) Notice: Subject to any disclaimer, the term of this patent is extended or adjusted under 35 U.S.C. 154(b) by 611 days.

(21) Appl. No.: 12/788,671

(22) Filed: May 27, 2010

(65) Prior Publication Data

US 2010/0324528 A1    Dec. 23, 2010

Related U.S. Application Data

(60) Provisional application No. 61/182,836, filed on Jun. 1, 2009.

(30) Foreign Application Priority Data

Jul. 10, 2009    (EP) ..................................... 09009054

(51) Int. Cl.
*A61M 5/00*    (2006.01)
(52) U.S. Cl.
USPC ............ 604/208; 604/207; 604/209; 604/211
(58) Field of Classification Search
USPC ................................................ 604/207–211
See application file for complete search history.

(56) References Cited

U.S. PATENT DOCUMENTS

| | | | |
|---|---|---|---|
| 3,302,462 A | 2/1967 | Pursell | |
| 5,423,752 A | 6/1995 | Haber et al. | |
| 5,514,097 A | 5/1996 | Knauer | |
| 5,584,815 A | 12/1996 | Pawelka et al. | |
| 5,591,136 A | 1/1997 | Gabriel | |
| 5,792,117 A | 8/1998 | Brown | |
| 5,820,602 A | 10/1998 | Kovelman et al. | |
| 6,090,080 A | 7/2000 | Jost et al. | |
| 6,936,032 B1 | 8/2005 | Bush, Jr. et al. | |
| 2004/0097883 A1* | 5/2004 | Roe ............................... | 604/207 |
| 2004/0127858 A1 | 7/2004 | Bendek et al. | |
| 2004/0162528 A1 | 8/2004 | Horvath et al. | |
| 2004/0186437 A1 | 9/2004 | Frenette et al. | |

(Continued)

FOREIGN PATENT DOCUMENTS

| DE | 93 01 334 U1 | 4/1993 |
|---|---|---|
| DE | 197 30 999 C1 | 12/1998 |

(Continued)

OTHER PUBLICATIONS

Machine Deisgn, Penton Media, vol. 65, No. 11 (1993) p. 36 "Standard Compression Springs Save Space".

*Primary Examiner* — Emily Schmidt
*Assistant Examiner* — Bradley G Thomas, Jr.
(74) *Attorney, Agent, or Firm* — McDonnell Boehnen; Hulbert & Berghoff LLP

(57)    ABSTRACT

A method and system for priming a drug delivery device. The drug delivery device includes a dose dial sleeve and an internal housing portion. The dose dial sleeve is coupled to the internal housing. The dose dial sleeve rotates on a substantially circumferential rotational path during priming of the drug delivery device. Further, the dose dial sleeve rotates on a helical path during dose setting of the drug delivery device.

14 Claims, 4 Drawing Sheets

(56) References Cited

U.S. PATENT DOCUMENTS

| | | |
|---|---|---|
| 2004/0210199 A1 | 10/2004 | Atterbury et al. |
| 2004/0236285 A1 | 11/2004 | Fisher et al. |
| 2005/0055011 A1* | 3/2005 | Enggaard .................. 604/500 |
| 2005/0137571 A1 | 6/2005 | Hommann |
| 2006/0153693 A1 | 7/2006 | Fiechter et al. |
| 2006/0258988 A1 | 11/2006 | Keitel et al. |
| 2007/0021718 A1 | 1/2007 | Burren et al. |
| 2008/0027397 A1 | 1/2008 | DeRuntz et al. |
| 2008/0077095 A1 | 3/2008 | Kirchhofer |
| 2008/0208123 A1 | 8/2008 | Hommann |
| 2009/0227959 A1* | 9/2009 | Hirschel et al. ............. 604/207 |
| 2009/0275916 A1* | 11/2009 | Harms et al. ............... 604/506 |

FOREIGN PATENT DOCUMENTS

| | | |
|---|---|---|
| DE | 298 18 721 U1 | 3/2000 |
| DE | 10 2005 063 311 A1 | 8/2006 |
| DE | 10 2005 060 928 A1 | 6/2007 |
| DE | 10 2006 038 123 A1 | 2/2008 |
| DE | 10 2007 026 083 A1 | 11/2008 |
| EP | 0 897 728 A1 | 2/1999 |
| EP | 0 937 471 A2 | 8/1999 |
| EP | 0 937 472 A2 | 8/1999 |
| EP | 1 541 185 A1 | 6/2005 |
| EP | 1 776 975 A2 | 4/2007 |
| EP | 1 923 084 A1 | 5/2008 |
| GB | 2 443 390 A | 5/2008 |
| WO | 92/18180 A1 | 10/1992 |
| WO | 93/07922 A1 | 4/1993 |
| WO | 96/23973 A1 | 8/1996 |
| WO | 96/39214 A1 | 12/1996 |
| WO | 97/10864 A1 | 3/1997 |
| WO | 99/03520 A1 | 1/1999 |
| WO | 01/19434 A1 | 3/2001 |
| WO | 03/080160 A1 | 10/2003 |
| WO | 2004/020028 A1 | 3/2004 |
| WO | 2004/064902 A1 | 8/2004 |
| WO | 2004/078241 A1 | 9/2004 |
| WO | 2004/078242 A2 | 9/2004 |
| WO | 2004/078293 A1 | 9/2004 |
| WO | 2005/018721 A1 | 3/2005 |
| WO | 2005/021072 A1 | 3/2005 |
| WO | 2005/044346 A2 | 5/2005 |
| WO | 2005/123159 A2 | 12/2005 |
| WO | 2006/024461 A1 | 3/2006 |
| WO | 2006/058883 A2 | 6/2006 |
| WO | 2006/079481 A1 | 8/2006 |
| WO | 2006/089767 A1 | 8/2006 |
| WO | 2006/114395 A1 | 11/2006 |
| WO | 2006/125328 A1 | 11/2006 |
| WO | 2007/017052 A1 | 2/2007 |
| WO | 2007/067889 A1 | 6/2007 |
| WO | 2008/031235 A1 | 3/2008 |
| WO | 2008/074897 A1 | 6/2008 |
| WO | 2008/116766 A1 | 10/2008 |
| WO | 2008/128373 A1 | 10/2008 |

* cited by examiner

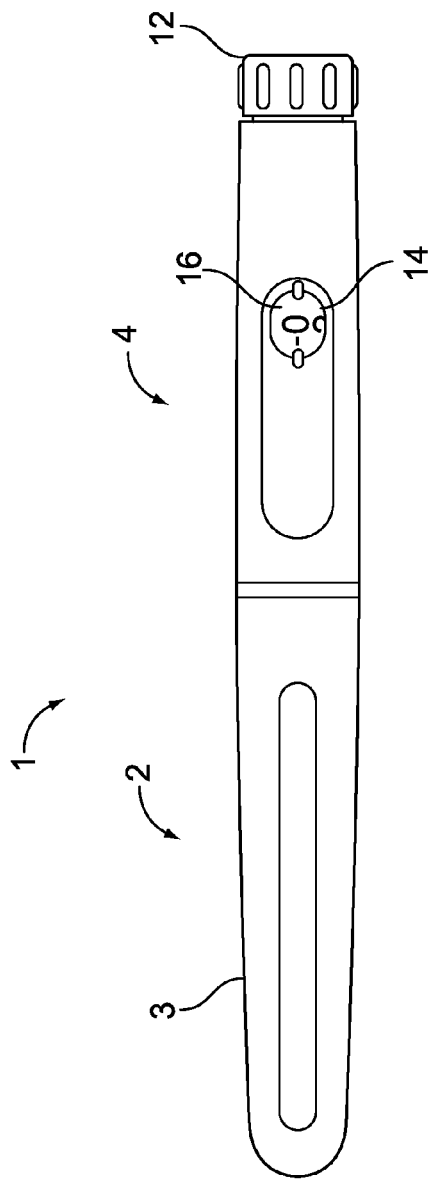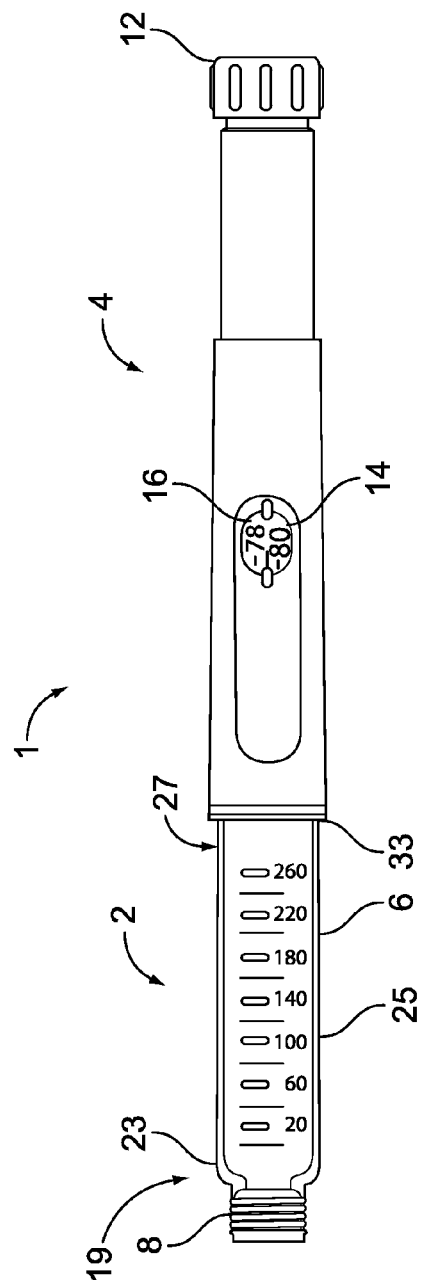

DOSE SETTING MECHANISM FOR PRIMING A DRUG DELIVERY DEVICE

FIELD OF THE PRESENT PATENT APPLICATION

The present patent application is generally directed to drug delivery devices. More particularly, the present patent application is generally directed to drug delivery devices, such as pen type drug delivery devices. Such devices provide for self administration of medicinal product from a multi-dose cartridge and permit a user to set the delivery dose. The present application may find application in both resettable (i.e., reusable) and non-resettable (i.e., non-reusable) type drug delivery devices. However, aspects of the invention may be equally applicable in other scenarios as well.

BACKGROUND

Pen type drug delivery devices have application where regular injection by persons without formal medical training occurs. This is increasingly common among patients having diabetes where self-treatment enables such patients to conduct effective management of their disease.

In certain types of medication delivery devices, such as pen type devices, cartridges of medication are used. These cartridges are housed in a cartridge holder or cartridge housing. Such cartridges include a bung or stopper at one end. At the other end of the cartridge, the cartridge comprises a pierceable seal. To dispense a dose of medication from such a cartridge, the medication delivery device has a dose setting mechanism that uses a spindle to move in a distal direction towards the cartridge and to press a distal end of the spindle against the bung. This expels a certain set dose of medication from the cartridge. In order to insure dose accuracy, it is important that the distal end of the spindle remains on the bung of the cartridge before, during and after injection of a dose of medicament.

One perceived disadvantage of certain known medication delivery devices is that because of the various tolerance differences that may occur during manufacturing (e.g., tolerance differences that may arise during component molding) of the various parts making up the drug delivery device and the desire to not pre-load the bung axially in the assembled device, there may be a gap between the end of the spindle and the cartridge bung when the medication delivery device is assembled. In other words, when initially assembled, the cartridge (and hence cartridge bung) may not be in contact with the distal end of the spindle. Therefore, if a user using the drug delivery device for the first time dials a dose, the actual dose received may be equal to the dialed dose less the initial gap between the distal end of the spindle and cartridge bung. The air gap between the cartridge bung and distal end of the spindle may be equivalent to a dose that causes the received dose that is outside preferred dose accuracy limits. For example, this air gap may be equivalent to the loss of between 0 and 10 units (i.e., 0-0.14 milliliters) of drug product on the first dose.

There is, therefore, a general need to take these perceived issues into consideration when designing either resettable or non-resettable drug delivery devices, such as pen type drug delivery devices.

SUMMARY

According to an exemplary arrangement, a dose setting mechanism for a drug delivery device is provided. The drug delivery device includes a dose dial sleeve and an internal housing portion. The dose dial sleeve is coupled to the internal housing. In this exemplary arrangement, the dose dial sleeve rotates on a circumferential rotational path during priming of the drug delivery device. Further, the dose dial sleeve rotates on a helical path during dose setting of the drug delivery device.

According to another arrangement, a method of priming a drug delivery device is provided. The method includes providing a dose dial sleeve engaged with an inner housing of a drug delivery device. The method also includes rotating the dose dial sleeve on a circumferential rotational path around the inner housing. In this exemplary arrangement, rotating the dose dial sleeve primes the drug delivery device.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 1 illustrates an arrangement of the drug delivery device in accordance with the one aspect of the present invention;

FIG. 2 illustrates the drug delivery device of FIG. 1 with a cap removed and showing a cartridge holder;

DETAILED DESCRIPTION

Figure 3:
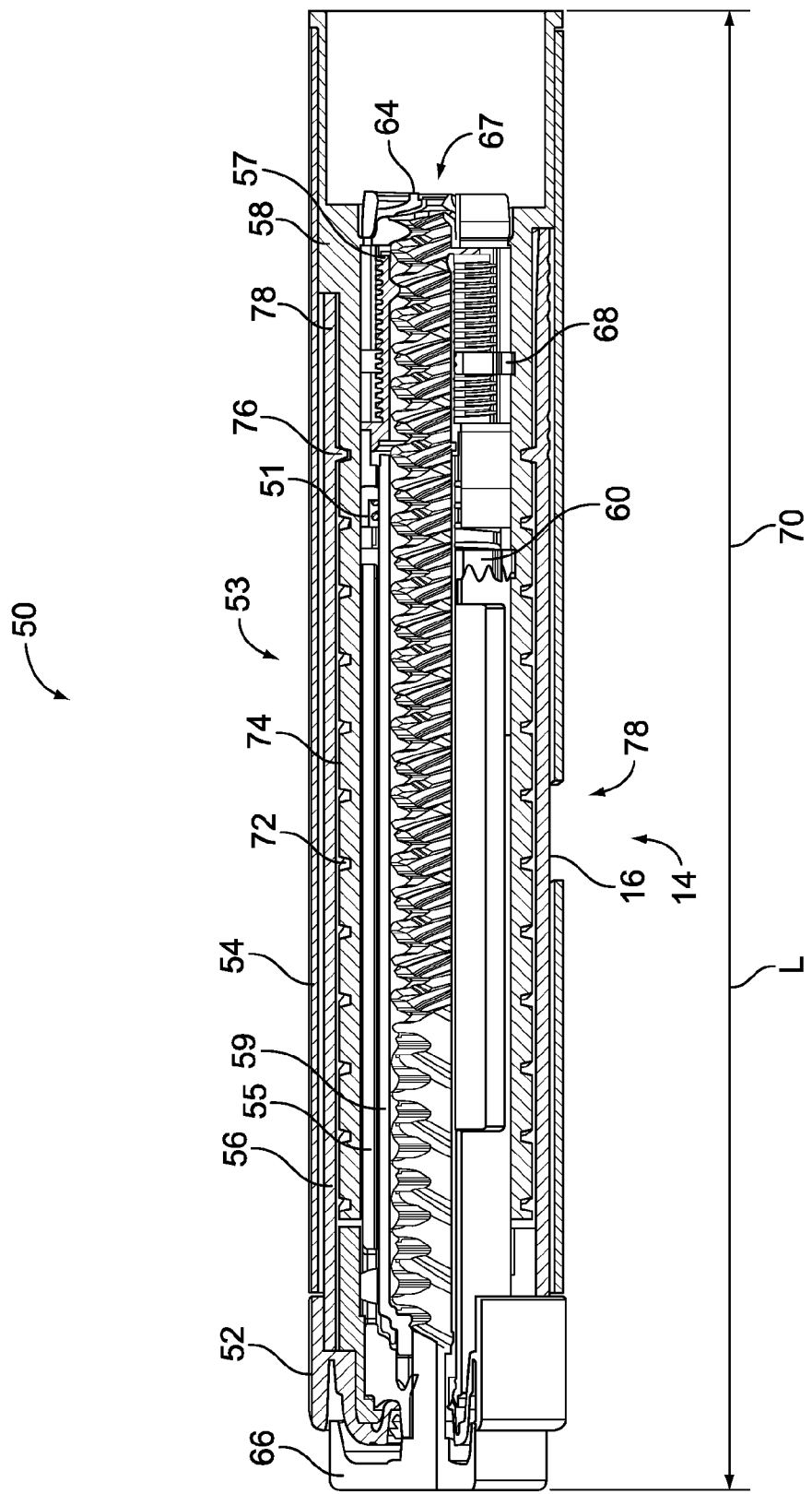
FIG. 3 illustrates a cross section view of an exemplary dose setting mechanism, such as the dose setting mechanism illustrated in FIG. 2.

Referring to FIG. 1, there is shown a drug delivery device 1 in accordance with an exemplary arrangement. The drug delivery device 1 comprises a housing having a first cartridge retaining part 2, and a dose setting mechanism 4. The drug delivery device may be a resettable drug delivery device (i.e., a reusable device) or alternatively a non-resettable drug delivery device (i.e., a non-reusable device). A first end of the cartridge retaining part 2 and a second end of the dose setting mechanism 4 are secured together by connecting features. For non-resettable devices, these connecting features would be permanent and non-reversible. For resettable devices, these connecting features would be releasable.

In this illustrated arrangement, the cartridge housing 2 is secured within the second end of the dose setting mechanism 4. A removable cap 3 is releasably retained over a second end or distal end of a cartridge retaining part or cartridge housing. The dose setting mechanism 4 comprises a dose dial grip 12 and a window or lens 14. A dose scale arrangement 16 is viewable through the window or lens 14. To set a dose of medication contained within the drug delivery device 1, a user rotates the dose dial grip 12 such that a dialed dose will become viewable in the window or lens 14 by way of the dose scale arrangement 16.

FIG. 2 illustrates the medical delivery device 1 of FIG. 1 with the cover 3 removed from a distal end 19 of the medical delivery device 1. This removal exposes the cartridge housing 6. As illustrated, a cartridge 25 from which a number of doses of a medicinal product may be dispensed, is provided in the cartridge housing 6.

Preferably, the cartridge 25 contains a type of medicament that can be administered relatively often, such as once or more times a day. One such medicament is either long acting or short acting insulin or an insulin analog. The cartridge 25 comprises a bung or stopper (not illustrated in FIG. 2) that is retained near a second end or a proximal end 33 of the cartridge 25. The medical delivery device also comprises a driver having a spindle (not illustrated in FIG. 2). As discussed above, before the device is primed, there may or may not be a gap between the end of the spindle and the cartridge bung.

The cartridge housing 6 has a distal end 23 and a proximal end 27. Preferably, the cartridge distal end 23 of the cartridge housing 6 comprises a groove 8 for attaching a removable needle assembly. However, other needle assembly connection mechanisms could also be used. If the drug delivery device 1 comprises a resettable device, the cartridge proximal end 27 is removably connected to the dose setting mechanism 4. In one preferred embodiment, cartridge housing proximal end 27 is removably connected to the dose setting mechanism 4 via a bayonet connection.

However, as those of ordinary skill in the art will recognize, other types of removable connection methods such as threads, partial threads, ramps and detents, snap locks, snap fits, and luer locks may also be used.

As previously mentioned, the dose setting mechanism 4 of the drug delivery device illustrated in FIG. 2 may be utilized as a reusable drug delivery device. (i.e., a drug delivery device that can be reset) Where the drug delivery device 1 comprises a reusable drug delivery device, the cartridge 25 is removable from the cartridge housing 6. The cartridge 25 may be removed from the device 1 without destroying the device 1 by merely having the user disconnect the dose setting mechanism 4 from the cartridge housing 6.

In use, once the cap 3 is removed, a user can attach a suitable needle assembly to the groove 8 provided at the distal end 23 of the cartridge housing 6. Such needle assembly may be, for example, screwed onto a distal end 23 of the housing 6 or alternatively may be snapped onto this distal end 23. After use, the replaceable cap 3 may be used to re-cover the cartridge housing 6. Preferably, the outer dimensions of the replaceable cap 3 are similar or identical to the outer dimensions of the dose setting mechanism 4 so as to provide an impression of a unitary whole when the replaceable cap 3 is in position covering the cartridge housing 6 when the device is not in use.

FIG. 3 illustrates a cross sectional view of a first arrangement of a disposable dose setting mechanism 50, such as the dose setting mechanism 4 illustrated in FIG. 2.

With reference to FIG. 3, the dose setting mechanism 50 comprises a dose dial grip 52, a spring 51, an outer housing 54, a clutch 55, a driver 53, a dial sleeve 56, a spindle 64 and an inner housing 58. In normal use, the operation of the dose setting mechanism 50 occurs as follows. To dial a dose, a user rotates the dose dial grip 52. The driver 53, the clutch 55 and the dial sleeve 56 rotate along with the dose dial grip. The dial sleeve 56 extends in a proximal direction away from the inner housing 58. In this manner, the driver 53 climbs the spindle 64. At the limit of travel, a radial stop on the dial sleeve 56 engages either a first stop or a second stop provided on the outer housing 54 to prevent further movement. Rotation of the spindle is prevented due to the opposing directions of the overhauled and driven threads on the spindle. A dose limiter 68, keyed to the outer housing 54, is advanced along the thread by the rotation of the driver 53.

When a desired dose has been dialed, the user may then dispense the desired dose of by depressing the dial grip 52. As the user depresses the dial grip 52, this displaces the clutch 55 axially with respect to the dial sleeve 56, causing the clutch 55 to disengage. However the clutch 55 remains keyed in rotation to the driver 53. The driver 53 is prevented from rotating with respect to the outer housing 54 but it is free to move axially with respect thereto. The longitudinal axial movement of the driver 53 causes the spindle to rotate and thereby to advance the piston in a cartridge.

In accordance with an exemplary arrangement, it may be beneficial to force a user to prime the drug delivery device of FIGS. 1 and 2 before the user dials and injects the first dose. In order to achieve this forced priming, as will be discussed in greater detail below, the dose setting mechanism 4 of drug delivery device 1 preferably forces a user to prime the device before setting the first dose.

Figure 4:
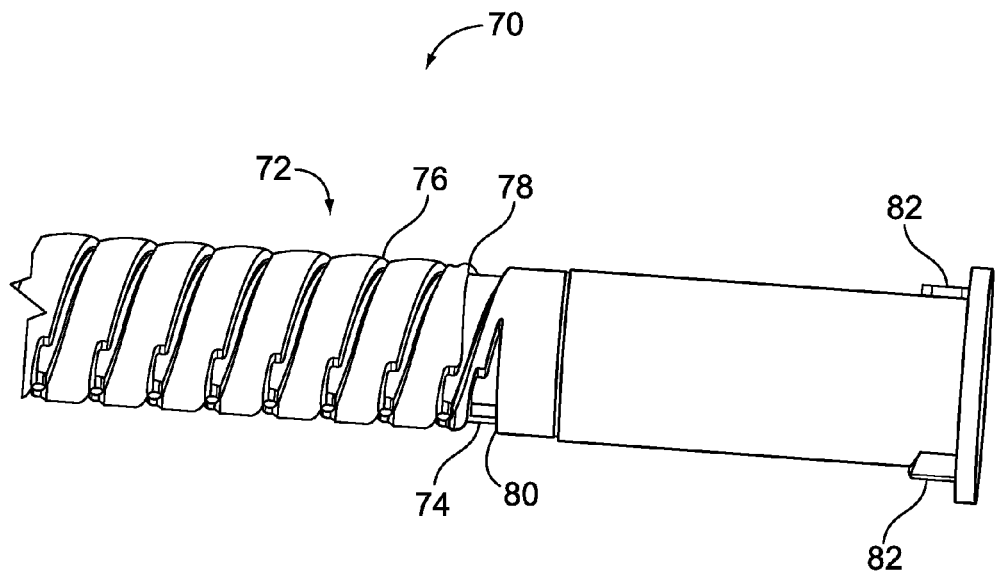
FIG. 4 illustrates a perspective view of an inner housing portion of a dose setting mechanism, such as the dose setting mechanism of FIG. 3.

As described above, the dose setting mechanism 50 comprises an inner housing 58 and a dial sleeve 56 that interact with one another to force a user to prime the device before dialing a first dose. FIG. 4 illustrates one arrangement of an inner housing 70, such as the inner housing 58 of the dose setting mechanism 50 illustrated in FIG. 3.

The inner housing 70 comprises a threaded portion 72. The threaded portion 72 includes a rotational threaded portion 74 and a helical threaded portion 76. The rotational threaded portion 74 may be defined by opposing faces 78 and 80. The rotational threaded portion defines a rotational path and the helical threaded portion defines a helical path. As will be discussed in more detail below, movement along the rotational path operates to prime the drug delivery device such that the spindle 64 (as illustrated in FIG. 3) is moved to an abutting position to a bung of a cartridge. In addition, movement along the helical path operates to set a dose of the dose setting mechanism (such as illustrated in FIG. 3).

The inner housing 70 further comprises at least one non-return element 82. The non-return element 82 may be a protrusion from the inner housing 70 and the protrusion may be various shapes. For instance, the non-return element 82 may be a raised substantially rectangular-shaped protrusion. It should be understood, however, the non-return element 82 could be a different shape. In an exemplary arrangement, the inner housing 70 also includes two non-return elements. However, the inner housing 70 may have any number of non-return elements. The non-return elements may be located at the distal end of the inner housing 70 or anywhere along its length.

Figure 5:
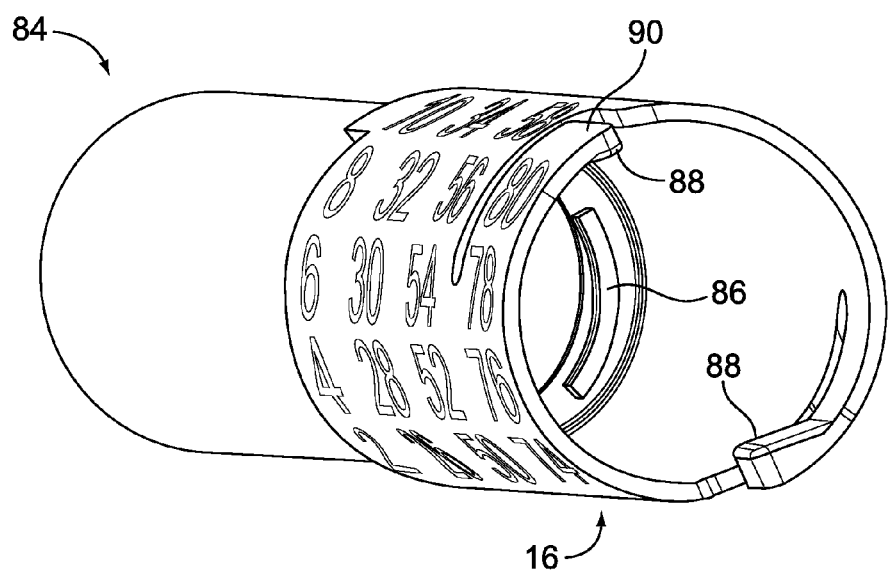
FIG. 5 illustrates a perspective view of a dose dial sleeve of a dose setting mechanism, such as the dose setting mechanism of FIG. 3.

FIG. 5 illustrates an arrangement of a dial sleeve 84, such as the dial sleeve 56 illustrated in FIG. 3. When assembled, the dial sleeve 84 is placed over the inner housing 70 and engages with the inner housing 70. As mentioned above, the dial sleeve 84 may be provided with a scale arrangement 16. The dial sleeve 84 also comprises a thread portion 86. This thread portion 86 is preferably an internal thread portion, as depicted. The internal thread portion 86 is capable of engaging with the threaded portion 72 of the inner housing 70. In particular, the internal thread portion is capable of engaging with both rotational threaded portion 74 and helical threaded portion 76.

The dial sleeve 84 further comprises at least one non-return element 88. In the exemplary arrangement, the non-return element 82 on the inner housing 70 is complimentary to the non-return element 88 on the dial sleeve 84. The non-return element may be a protrusion from the dose dial sleeve. In an exemplary arrangement, the non-return element 88 is connected to a flexible element 90 of the dial sleeve 84.

As depicted, the flexible element 90 may be created by a slit in the dial sleeve 84. It should be understood, however, that the flexible element may be formed in different ways. For example, the dose dial sleeve may be manufactured from flexible material. As will be described in greater detail below, this flexible element 90 preferably allows for the non-return element 88 to pass over the complimentary non-return element 82 of the inner housing 70 when the dial sleeve travels through the rotational path defined by the rotational threaded portion.

When the dose dial sleeve 84 and inner housing 70 are engaged, these elements operate as a dose setting mechanism that forces a user to prime the device before a user can set a first dose. In particular, the dial sleeve 84 must travel on a path along the rotational threaded portion 74 before the dial sleeve can travel along the helical threaded portion 76. As this dose setting mechanism forces a user to prime the device, the dose setting mechanism described does not suffer from the drawback of possibly dispensing an incorrect dose due to the initial separation between the spindle 64 and the cartridge bung.

Figure 6:
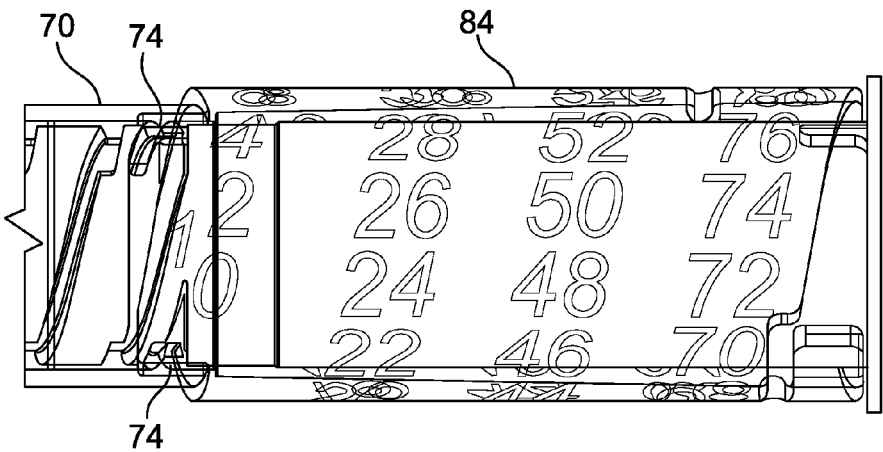
FIG. 6 illustrates a perspective view of the dose dial sleeve coupled to the inner housing before priming of a dose setting mechanism, such as the dose setting mechanism illustrated in FIG. 3.

The operation of the dose setting mechanism will be further described with reference to FIGS. 6-8. FIG. 6 illustrates a dose setting mechanism before priming of the drug delivery device. As depicted, internal thread 86 of dial sleeve 84 is engaged with rotational threaded portion 74 of inner housing 70. A user must first rotate the dial sleeve 84 along a path that is substantially rotational. During the rotational movement, the dial sleeve rotates along a circumferential or circular path. The movement is limited to movement that is substantially rotational and the dial sleeve does not move axially across the inner housing 70 (i.e., the dial sleeve does not translate).

This circumferential rotational movement acts to prime the drug delivery device. As illustrated in the exemplary dose setting mechanism illustrated in FIG. 3, the drug delivery device 1 (or, more particularly, the dose setting mechanism 50) may comprise a driver 53 and a spindle 64. The dose dial sleeve 84 may be coupled to the driver.

Further, as described with reference to FIG. 1, the drug delivery device may comprise a cartridge housing which houses a cartridge from which a number of doses of a medicinal product may be dispensed. This cartridge housing may be coupled to the dose setting mechanism 50. The movement of the dose dial sleeve 84 along the rotational threaded portion may also cause the driver to rotate. This rotation of the driver may cause the spindle to advance towards the cartridge in the cartridge housing.

This advancement of the spindle removes any potential initial separation between the spindle and the cartridge bung. In other words, this advancement of the spindle caused by the rotation of the dose dial sleeve and driver primes the drug delivery device. Although the exemplary dose setting mechanism 50, as illustrated, is a disposable dose setting mechanism, one of skill in the art will recognize that such dose setting mechanism may be modified so as to be used as a reusable or resettable dose setting mechanism.

If a user attaches a needle to the drug delivery device 1 before the user primes the device, then a small amount of drug may be expelled during the priming operation. Alternatively, if the user attaches the needle after priming the device or after setting the first dose, then the drug, which will be pressurized from the priming, will be expelled as the needle is connected to the drug delivery device. Accordingly, the drug amount resulting from the priming operation will be expelled before the needle is inserted into a user's skin.

Figure 7:
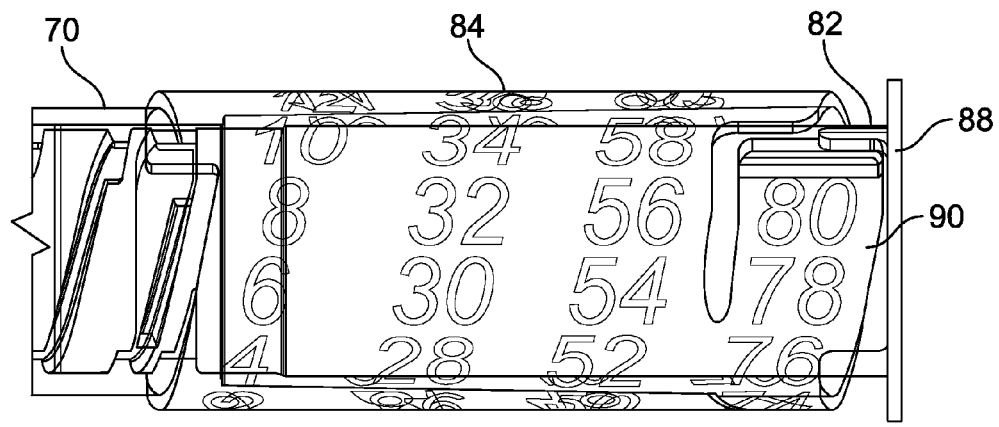
FIG. 7 illustrates a perspective view of the dose dial sleeve coupled to the inner housing after priming of a dose setting mechanism, such as the dose setting mechanism illustrated in FIG. 3.

FIG. 7 illustrates the dose setting mechanism after priming of the drug delivery device has occurred. As shown, the rotational threaded portion 74 of the inner housing 70 defines a substantially rotational path that ends when the internal thread 86 on the dose dial sleeve makes contact with the start of the helical thread 76 on the inner housing. When the dose dial sleeve reaches the end of the rotational path or substantially the end of the rotational path, the non-return element 82 of the inner housing and the non-return element 88 of the dial sleeve interact to prevent substantial movement back along the rotational path towards the original start positon. In particular, the non-return element 88 prevents the dose dial sleeve from rotating back past the non-return element 82. In other words, the non-return elements interact to prevent movement along the portion of the rotational path the dose dial sleeve traveled during the priming of the drug delivery device.

As can be seen by comparing FIGS. 6 and 7, during the priming operation (i.e., the rotational movement of the dial sleeve), the non-return element 88 of the dial sleeve is able to travel over the non-return element 82 of the inner housing. In addition, the flexible element 90 of the dial sleeve allows the non-return element 88 to pass over the non-return element 90. However, at the end of the rotational path and after the non-return elements pass one another, the flexible element snaps down towards the inner housing, as depicted in FIG. 7. When the flexible element snaps down, the non-return elements 82 and 88 abut one another and prevent the dose dial sleeve from going back on the rotational path it traveled during the priming of the device.

After priming, if a user of the device attempted to move the dose dial sleeve on the rotational path, the movement would be prevented because the non-return element 88 on the dose dial sleeve will not overcome the non-return element 82 on the inner housing.

Figure 8:
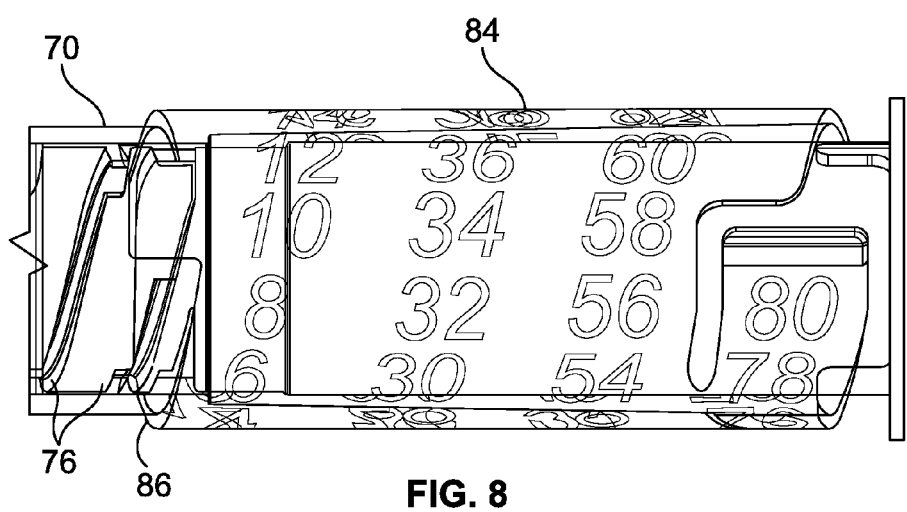
FIG. 8 illustrates a perspective view of the dose dial sleeve coupled to the inner housing during dose setting of a dose setting mechanism, such as the dose setting mechanism illustrated in FIG. 3.

FIG. 8 illustrates the dose setting mechanism during dose setting of the drug delivery device. FIG. 8 depicts the dose setting mechanism where approximately two units have been dialed. As can be seen, when a dose is being dialed, the internal thread 86 of the dial sleeve engages with the helical threaded portion 76 of the inner housing.

The drug delivery device is designed such that during dose setting, the dose dial sleeve travels on a helical path defined by the helical threaded portion. The dose dial sleeve cannot engage this helical thread until the dose dial sleeve has been rotated along the rotational thread of the inner housing. Accordingly, a user cannot dial a first dose until the user has primed the device.

In an exemplary arrangement, the drug delivery device may be designed to indicate to a user whether the device needs to be primed or does not need to be primed before dialing a dose. For instance, dose dial sleeve 84 may comprise a graphic printed on it that is displayed in the dose window before the pen is primed. The graphic may display a character such as "P" or a phrase such as "Priming Needed." Other graphics are possible as well. Once a device has been primed, the graphic will no longer be displayed in the dose window.

Further, since the non-return elements prevent the dose dial sleeve from returning back on the rotational path after priming, the user does not have to prime the device prior to a subsequent dose. Accordingly, a dose setting mechanism in accordance with an exemplary embodiment forces a user to prime the device before the first dose is dialed, but does not force the user to prime the device for subsequent doses.

However, in the event that the drug delivery device is reusable, it should be understood that a dose setting mechanism in accordance with an exemplary embodiment is designed so that the dose setting mechanism forces a user to prime the device each time a cartridge is replaced. In such a reusable device, the device is preferably designed so that a user could overcome the non-return elements. This may be accomplished, for example, by rotating the dose dial sleeve over a detent in the dialed position. This rotation would rotate the number sleeve back along the rotational path. Other ways for overcoming the non-return elements are possible as well.

Further, in this exemplary embodiment, it may be advantageous to force the user to do this before being able to remove the cartridge holder.

Exemplary embodiments of the present invention have been described. Those skilled in the art will understand, however, that changes and modifications may be made to these embodiments without departing from the true scope and spirit of the present invention, which is defined by the claims.

We claim:

1. A dose setting mechanism for a drug delivery device comprising: a dial sleeve; and an internal housing portion having; an outer surface comprising; a helical path, wherein the dial sleeve surrounds and is coupled to the internal housing portion, wherein the internal housing; portion is configured to allow the dial sleeve to rotate rotates along a substantially rotational path during priming of the drug delivery device, and wherein the dial sleeve translates along the a helical path during dose setting of the drug delivery device; the outer surface of the internal housing comprises a threaded portion, and wherein the threaded portion comprises a rotational threaded portion and a helical threaded portion; and the dial sleeve rotates on the rotational threaded portion during priming of the drug delivery device, and wherein the dial sleeve translates along the helical threaded portion during dose setting of the drug delivery device.

2. The invention of claim 1, wherein the dial sleeve is prevented from rotating on the helical path prior to the priming of the drug delivery device.

3. The invention of claim 1, further comprising at least one non-return element disposed on the dial sleeve.

4. The invention of claim 3, further comprising at least one complimentary nonreturn element disposed on the internal housing portion that is complimentary to the at least one non-return element disposed on the dial sleeve.

5. The invention of claim 4, wherein the substantially rotational path comprises an end of the rotational path, wherein, when the dial sleeve substantially reaches the end of the rotational path, the at least one non-return element and the at least one complimentary non-return element interact to prevent substantial movement of the dial sleeve back along the rotational path.

6. The invention of claim 4, wherein the non-return element is a protrusion from the dial sleeve, and wherein the complimentary non-return element is a protrusion from the internal housing.

7. The invention of claim 6, wherein the non return element is connected to a flexible element portion of the dial sleeve, wherein the flexible element allows for the non-return element to pass over the complimentary non-return element during the rotational movement, and wherein, at the end of the substantially rotational path, the flexible element operates to prevent the non-return element to pass back over the complimentary non-return element.

8. The invention of claim 1, wherein the dose setting mechanism is coupled to a cartridge housing.

9. The invention of claim 8, wherein the dose setting mechanism and cartridge housing are coupled via a non-reversible coupling.

10. The invention of claim 1, wherein the dial sleeve comprises a graphic that is displayed prior to the priming, wherein the graphic indicates that the drug delivery device has not been primed.

11. The invention of claim 1, wherein the dose setting mechanism further comprises:
a driver; and
a spindle, wherein the dial sleeve is operatively coupled to the driver, such that rotation of the dial sleeve causes the driver to rotate and the spindle to translate in a distal direction, this translation priming the drug delivery device.

12. The invention of claim 1, wherein the drug delivery device is non-reusable.

13. The invention of claim 1, wherein the drug delivery device is reusable.

14. The invention of claim 13, further comprising:
at least one non-return element disposed on the dose dial sleeve;
at least one complimentary non-return element disposed on the internal housing portion that is complimentary to the at least one non-return element disposed on the dose dial sleeve,
wherein, when a user is setting a dose, the non-return element and complimentary non-return element prevent substantial rotational movement along the substantially circumferential rotational path, and
wherein, when the user is not setting a dose, the non-return element and complimentary non-return element are capable of being overcome by a user of the device.

* * * * *